(12) United States Patent
Leijssen et al.

(10) Patent No.: US 7,884,330 B2
(45) Date of Patent: Feb. 8, 2011

(54) DETECTION MODULE

(75) Inventors: Jacobus Josephus Leijssen, Eindhoven (NL); Harry Marinus, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 246 days.

(21) Appl. No.: 12/094,409

(22) PCT Filed: Nov. 9, 2006

(86) PCT No.: PCT/IB2006/054177
§ 371 (c)(1),
(2), (4) Date: May 21, 2008

(87) PCT Pub. No.: WO2007/057820
PCT Pub. Date: May 24, 2007

(65) Prior Publication Data
US 2008/0258048 A1    Oct. 23, 2008

(30) Foreign Application Priority Data
Nov. 21, 2005 (EP) .................... 05111000

(51) Int. Cl.
*G01T 1/164* (2006.01)
*G01J 1/44* (2006.01)
(52) U.S. Cl. .............. 250/363.03; 250/214 L

(58) Field of Classification Search ............ 250/363.03, 250/208.1, 214 A, 214 L, 214 R; 600/407, 600/425
See application file for complete search history.

(56) References Cited

U.S. PATENT DOCUMENTS

| 5,692,511 | A  | * | 12/1997 | Grable ..................... 600/425 |
| 6,230,045 | B1 |   | 5/2001  | Hoogenraad et al. |
| 6,331,700 | B1 |   | 12/2001 | Wake et al. |
| 6,339,216 | B1 |   | 1/2002  | Wake |
| 6,681,130 | B2 | * | 1/2004  | Wake et al. ................ 600/407 |
| 7,495,202 | B2 | * | 2/2009  | Schrey et al. ........... 250/214 R |
| 2002/0060284 | A1 |   | 5/2002 | Mizuno et al. |

FOREIGN PATENT DOCUMENTS

| WO | WO9707529 A1 | 2/1997 |
| WO | WO9927343 A2 | 6/1999 |
| WO | WO03069287 A1 | 8/2003 |
| WO | WO03077724 A2 | 9/2003 |

* cited by examiner

*Primary Examiner*—David P Porta
*Assistant Examiner*—Faye Boosalis

(57) ABSTRACT

A detection module for detecting electro-magnetic radiation comprises a photosensor, a current integration circuit and an arithmetic unit fits the integration samples to a predetermined time dependency of the integrated current and computes an accumulated electrical charge accumulated over the integration time interval from the fit. Notably, the detection module is employed in an optical imaging apparatus to image e.g. a woman's breast by way of near-infrared light.

17 Claims, 5 Drawing Sheets

DETECTION MODULE

The invention pertains to a detection module for the detection of electro-magnetic radiation which comprises a photosensor with a current integration circuit. The invention also pertains to an apparatus for imaging a turbid medium.

The international application WO2003/077724 shows an optical tomographic scanning apparatus with a detector system.

The known optical tomographic scanning apparatus is designed to image a woman's breast. Accordingly the known optical tomographic scanning apparatus forms an apparatus for imaging a turbid medium formed by the breast tissue. The known optical tomographic scanning apparatus is provided with an near-infrared (nir) laser to illuminate the woman's breast to be examined. A detector system is orbited around the breast to detect nir-light transmitted through and re-emitted by the breast from several angular positions in the orbit. The detector system is provided with a photodiode to convert the incident light into an electrical output current. This known detector system integrates the output electrical current from the photodiode successively at several different integration intervals of successively longer lengths. Then, the values obtained at the end of the respective integration intervals are digitised. This approach amounts to oversampling or multiple sampling by repeatedly digitising the output electrical current from the photodiode. These multiple samplings are averaged to improve the signal-to-noise ratio of the averaged signal. In the averaged signal quantisation errors are reduced. Such quantisation errors have the effect that is like additive noise.

An object of the invention is to provide a detection module for detection of electromagnetic radiation of which the output has a high signal-to-noise ratio especially at low intensities of the incident electro-magnetic radiation. Also an object of the invention is provide a detection module for detection of electromagnetic radiation which does not require long signal acquisition and/or signal processing time.

This object is achieved by the detection module for detecting electro-magnetic radiation of the invention which comprises a photosensor to derive an electrical current from incident electro-magnetic radiation a current integration circuit to (i) integrate the electrical current from the photosensor over an integration time interval and (ii) to acquire several integration samples of time-integrated current during the integration time interval and an arithmetic unit to (i) fit the integration samples to a predetermined time dependency of the integrated current (ii) compute an accumulated electrical charge accumulated over the integration time interval from the fit and (iii) supply an output intensity signal that represents the accumulated electrical charge.

The detection module to detect electro-magnetic radiation of the invention takes multiple samples of the time-integrated electrical current from the photosensor. Thus the detection module by way of its current integration circuit tracks the accumulation of electrical charge are electrical current is being integrated over the integration time interval. These multiple samples are fit to the predetermined time dependency of the time-integrated electrical current. This predetermined time dependency is determined by the design of the photosensor and the time-dependency of the intensity of the incident radiation. On the basis of this information the predetermined time dependency of the time-integrated electrical current can be modelled in the form of a parameterised mathematical function. Thus, a mathematical model is provided that accurately represents the actual values of the time dependent time-integrated current as the integration time interval progresses. In many practical situations the intensity of the incident is about constant over the integration time interval. This situation notably occurs when the integration time interval is much shorter than the typical time scale of the variation of the intensity of the incident electro-magnetic radiation. For example, a linear approximation has provide accurate results for an integration interval having a time length of 10-100 ms. On the other hand, when the temporal variation of the intensity of the incident electro-magnetic radiation is predetermined or can be accurately estimated, the time-dependence of the intensity can be included in the mathematical model. The actual details of the mathematical function, i.e. one or several of its parameters are obtained by applying a fit procedure on the basis of the predetermined time dependency to the sampled values. Then the accurate value of the time-integrated electrical current as accumulated over the integration time interval is simply computed as the value of the actual time-dependency from the fit at the end point of the integration time interval. The fit procedure suppresses errors due to electronic noise, photon shot noise and digitisation errors and the like, since the entire accumulation of electrical current as the integration time interval progresses is taken into account. Notably, the fit procedure takes into account a substantial part of the accumulation of electrical current during the integration time interval, rather than just relying on the accumulated value sampled at the end point of the integration time interval. Experiments have shown that the detection module of the invention actually achieves a very low noise floor of less than 10 fA ($10 \cdot 10^{-15}$ A). Accordingly, the detection module of the invention is able to accurately measure very low electrical currents of less than 25 fA with a good signal-to-noise ratio. For example a root-mean-square (rms) noise of less than a fA (i.e. below $10^{-15}$ A) is achieved. Notably, noise in the integrated electrical current is amplified by impedance gain due to an operational amplifier that is employed in the current integration circuit. The present invention by way of the fit to linear increase with time of the integrated electrical current eliminates or effectively reduces this noise. Additionally the invention reduces the effect of variations in offset which may be caused by electrical drift in the current integration circuit and due to variations in electrical charge left behind after resetting a collecting capacitor of the current integration circuit. Also offset variations may be connected with variations of dark current in the photosensor, and dependencies upon the offset voltage over the photosensor.

Since the multiple sampling of the time-integrated electrical current is done within one integration time interval, there is no need to for a long measurement time and no successive averaging is needed for an individual measurement of the accumulated electrical charge that is representative for the incident intensity of the electro-magnetic radiation during the integration time interval.

According to a further aspect of the invention the detection module is provided with a synchronisation circuit that has the functions to monitor a disturbance source and to control or e.g. trigger the integration of the electrical current from the photosensor on the basis of the monitored phase of the disturbance source. There are several examples of such disturbance sources, notably switched mode power supplies and fields generated by a mains power source are abundantly present and may disturb the operation of the detection module especially when measuring extremely low electrical currents. The synchronisation circuit is for example especially adapted to initiate the sampling of the time-integrated current when the disturbance is low or even absent. In another example, the synchronisation circuit triggers the sampling of the time-integrated current at a particular phase of the disturbance for repeatedly detecting electro-magnetic radiation. In another example the synchronisation circuit controls the arithmetic circuit to perform a correction for the monitored disturbance. It appears that especially when detecting very low electrical current, synchronisation of the sampling further improves the signal-to-noise ratio of the output intensity signal. The noise level is effectively reduced into the range of 1 pA to 1 fA; even results of a very low noise level of less than 1 pA may be achieved.

According to a particular aspect of the invention the pre-determined time-dependency of the integrated electrical current is linear. This linear dependency is very simple and has appeared to be quite accurately represents the time-integrated electrical current as output from present day commercially available photosensors. On the basis of the linear dependency the accumulated electrical charge is easily calculated from the slope of the linear dependency as found from the fit and the duration of the integration time interval. Moreover, for the simple linear dependency of the integrated current only a low amount of data needs to be transferred to the arithmetic unit. This can be achieved by inexpensive low power components. Moreover, no additional signal transmission bandwidth is required to transfer and process the simple datasets.

According to a further aspect of the invention the current integration circuit the number of samples acquired for an individual measurement in the range of typically 400-500 samples in an individual integration interval.

The invention also pertains to an apparatus for imaging a turbid medium. An example of such an apparatus is an imaging system for optical or notably near-infrared imaging of a woman's breast. Imaging of this kind of turbid medium, notably human biological tissue is possible in a wavelength range of 50 nm to 1.4 μm, very good results are achieved in the wavelength range of 650-900 nm and excellent results are achieved in the range of 700-800 nm. The choice of wavelength ranges depends on consideration of low scatter (i.e. which increases at shorter wavelength) low absorption (which increases at high wavelength) and the absence of particular absorption bands due to e.g. oxygenated or non-oxygenated blood, etc. It has appeared that the breast tissue optically behaves as turbid because of multiple scatter of the light that progresses through the breast tissue. The imaging apparatus of the invention comprises a examination space to receive the turbid medium. In practice the examination space for example has the form of a chamber that is open at it upper end and into which the woman's breast be suspended from above into the opening of the chamber while the woman is comfortably positioned face down (that is, in prone position) over the chamber. Often a matching fluid is applied to surround the breast suspended into the chamber to avoid strong optical transitions at the edge of the breast. The use of the matching fluid strongly reduced artifacts in the reconstructed image of the breast being examined.

Electro-magnetic radiation from the breast is measured by electro-magnetic radiation detection modules located at or near the walls of the chamber. Alternatively, one or several electro-magnetic radiation detection modules may orbit around the examination space. The electro-magnetic radiation detection modules detect electro-magnetic radiation from the examination space from several orientations. In one aspect of the imaging apparatus the breast may be illuminated by sources that are located around the examination space or that orbit around the examination space in order to irradiate the turbid medium, i.e. the woman's breast, from several orientations. In another aspect of the imaging apparatus of the invention a contrast agent is administered to the patient to be examined which cause fluorescence from the breast tissue, where notably fluorescence is enhanced in tumour tissue. For example the fluorescence enhancement is due to increased concentration of contrast agent that is due to preferred accumulation of contrast agent in tumour tissue.

The imaging apparatus of the invention is provided with one or more electro-magnetic radiation detection modules of the invention as disclosed above. The electro-magnetic radiation detection modules are employed in the imaging apparatus of the invention to detector electro-magnetic radiation, notably optical or near-infrared radiation from the turbid medium, notably the woman's breast. These one or more electro-magnetic radiation detection modules supply output intensity signals that represent the accumulated electrical charges that in turn are representative of the radiation intensities as observed from respective orientations from the examination zone. These output intensity signals are applied to a reconstructor which reconstructs one or several images of the turbid medium, i.e. the woman's breast. Several reconstructions algorithms are available for reconstructing two-dimensional or three-dimensional image datasets.

The detection modules of the invention generate the output intensity at a very good signal-to-noise ratio, especially at very low intensity levels. Hence, reconstruction artifacts in the reconstructed image are avoided so that the reconstructed image has a high diagnostic quality in that small details with little contrast are nevertheless rendered well visible.

These and other aspects of the invention will be further elaborated with reference to the embodiments defined in the dependent Claims.

These and other aspects of the invention will be elucidated with reference to the embodiments described hereinafter and with reference to the accompanying drawing wherein FIG. 1 shows a schematic diagram of the apparatus for imaging a turbid medium of the invention;

Figure 1:
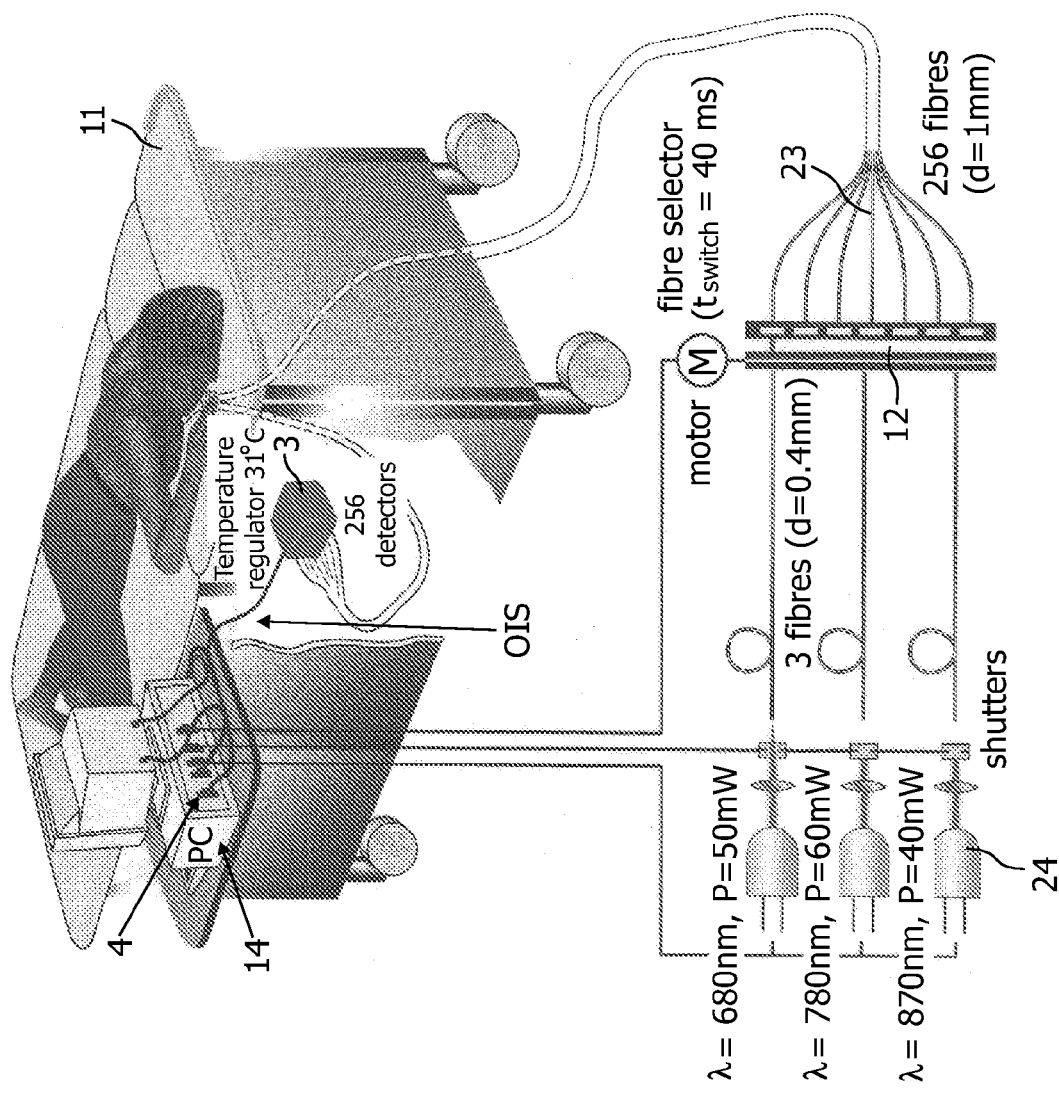

FIG. 1 shows a schematic diagram of the apparatus for imaging a turbid medium of the invention. Notably, the apparatus for imaging a turbid medium shown diagrammatically in FIG. 1 is an optical mammography system. The optical mammography system comprises a carrier 11 on which the patient to be examined (notably a woman whose breast(s) 1 are to be examined is placed in prone position (i.e. face down) having one breast suspended in the examination space 2 that has to form of a measurement cup 2 (see FIG. 2). The space between the breast 1 and the cup surface is filled with a scattering fluid 22, which scattering properties for example closely match the scattering properties of the average breast so that transitions of optical properties between the breast tissue and space outside the breast are reduced.

Figure 2:
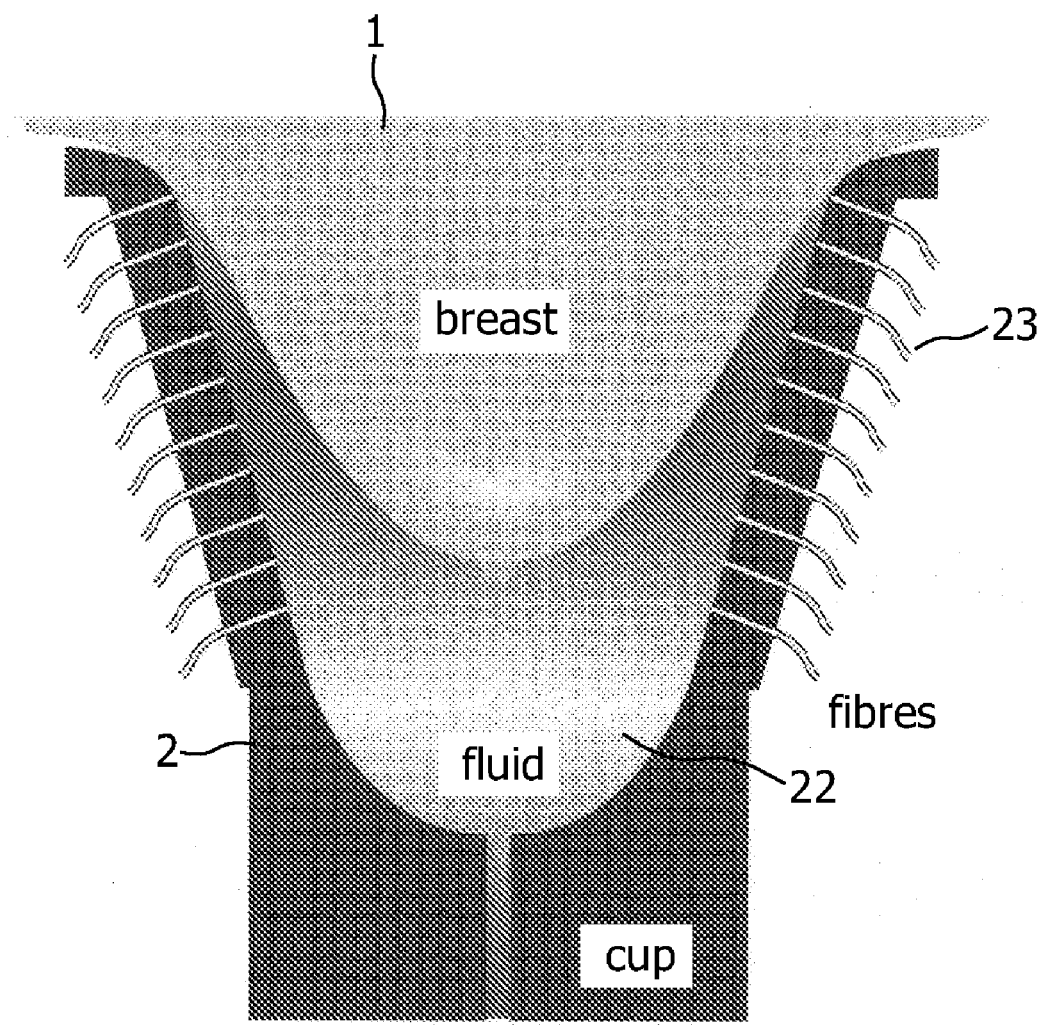
FIG. 2 shows a schematic cross-sectional drawing of the cup with a turbid medium in the form of a breast.

FIG. 2 shows a schematic cross-sectional drawing of the cup with a breast 1.

A large number of fibres 23 (510 in total) is connected with one end to the cup. Half of the fibres are connected to detector modules 5 with the other end, and half of the fibres are connected to a fibre-switch 12 with the other end. The fibre-switch 12 can direct light from three different lasers 24 in either one of the 256 source fibres 23 (255 to the cup, one directly to a detector fibre). In this way, either one of the source fibres 23 can provide a conical light beam in the cup. By properly switching the fibre-switch 12, all the source fibres will emit a conical light beam subsequently.

The light from the selected source fibre is scattered by the scattering fluid and the breast, and is detected by the 255 detector modules. The scattering of light in breast tissue is strong, which means that only a limited amount of photons can transverse the breast, compared to the reflected (or back-scattered) light. Therefore, a large dynamical range should be covered by the detectors (about 9 orders of magnitude). Photodiodes are used as photosensors 5 in the detector modules. The front-end detector electronics includes of these photodiodes and an amplifier 31. The amplification factor of the amplifier can be switched between several values. The machine first measures at the lowest amplification, and increases the amplification if necessary. The detectors are controlled by a computer 14.

This computer 14 also controls the lasers, the fibre-switch, and the pump system. The computer, cup, fibres, detectors, fibre-switch, and the lasers are all mounted into a bed as shown in FIG. 2.

A measurement starts with a cup 2 filled completely with the scattering fluid 22, this is the calibration measurement. After this calibration measurement, a breast 1 is immersed in the fluid, and the measurement procedure is carried out again. Both the calibration and the breast measurement consist of 255'255 detector output intensity signals (OIS) for each of the three lasers 24. These detector output intensity signals (OIS) can be converted into a three dimensional image using a process called image reconstruction. The image reconstruction of the image of the breast from the is carried out by a reconstructor 4 that is usually implemented in software in the computer 14. The reconstruction process, which is based on for example an algebraic reconstruction technique (ART) or finite element method (FEM), finds the most likely solution to the (ill-defined) inverse problem.

Figure 3:
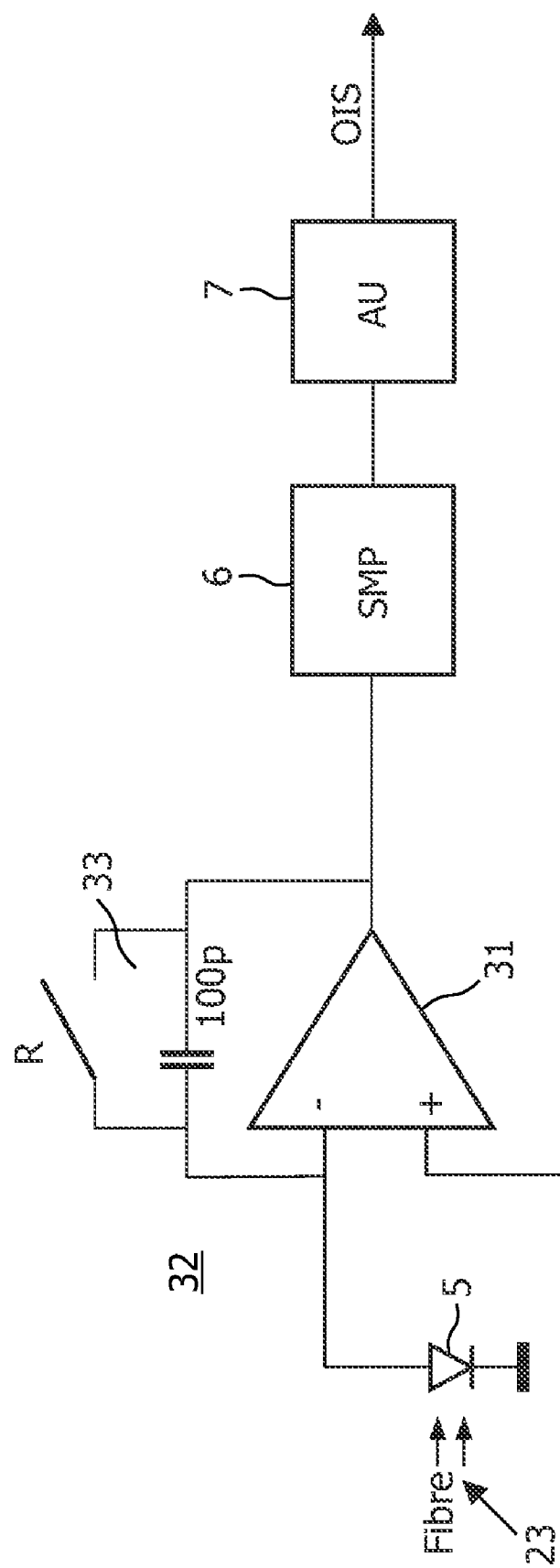
FIG. 3 shows an electric circuit diagram of the detection module of the invention for detecting electro-magnetic radiation.

FIG. 3 shows an electric circuit diagram of the detection module of the invention for detecting electro-magnetic radiation. The detection module includes in integrator circuit 32 that includes an operational amplifier 31 and a capacitance 33 in parallel. Further a reset switch R is in parallel with the capacitance 33. The integration circuit receives the photocurrent from the photodiode 5. The integrated photodiode current is sampled during the integration period of for example 120 ms for about 460 times by the sampling unit 6, for example a 24-bit ADC may be employed as the sampling unit. The integration samples from the sampling unit are applied to the arithmetic unit which fits the integration samples to a linear time dependence (see FIG. 4). From the result of the at fit the output intensity signal is computed as the value of the fitted linear dependency at the end of the integration time interval, i.e. at 120 ms.

The fit procedure is now presented in some detail.

The linear dependency of the integrated electrical current with time during the integration time interval is given as: y=bx+a a=offset (don't care) and b=gradient or slope. This parameters are computed as $$\begin{cases} a = \dfrac{(\Sigma y)(\Sigma x^2) - (\Sigma x)(\Sigma xy)}{n\Sigma x^2 - (\Sigma x)^2} \\ b = \dfrac{n\Sigma xy - (\Sigma x)(\Sigma y)}{n\Sigma x^2 - (\Sigma x)^2} \end{cases}$$

-continued

Where $\sum$ stands for $\sum_{i=1}^{n} \ldots i$

This calculation is done "on the fly" during each ADC sample interrupt.

Figure 4:
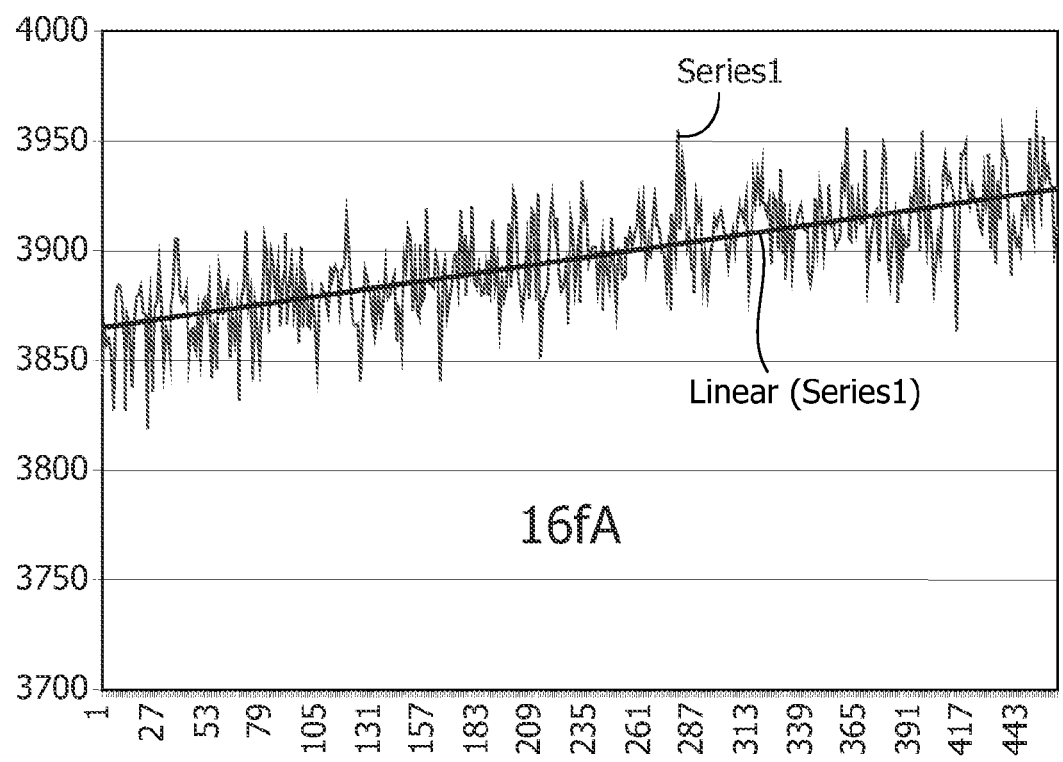
FIG. 4 shows a sampled integrated photocurrent of 16 fA.

FIG. 4 shows a sampled integrated photocurrent of 16 fA. The photocurrent is integrated and sampled 460 times during the 120 ms integration time interval. This leads to the rather noise curve. To this noisy curve a linear fit is drawn and the accumulated electrical charge over the integration time interval is computed as the value of the linear fit at the end point of the integration time period, i.e. at 120 ms. This fit involves only two scalar parameters namely the slope of the linear dependency and its offset at the start of the integration time interval.

Figure 5:
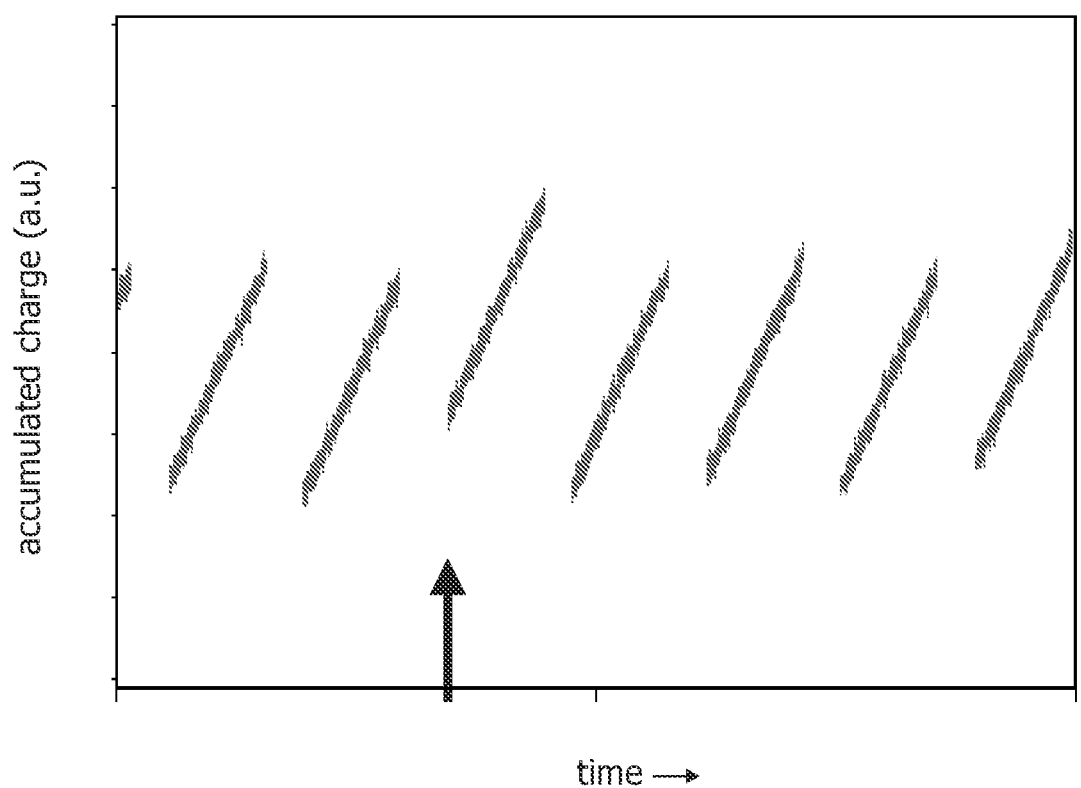
FIG. 5 shows results from experiments on several individual integration intervals.

FIG. 5 shows results from experiments on several individual integration intervals. Notably, FIG. 5 represents the several repeats of the integration of the electrical current from the photosensor. Each individual somewhat noisy streak represents an individual integration. As FIG. 5 show, the offset at the beginning of each individual integration may change. However, the fit according to the invention to a linear time dependency reduces of even eliminates the effect of this variation of the offset on the computed accumulated electrical charge.

The invention claimed is:

1. A detection module for detecting electro-magnetic radiation comprising
   a photosensor to derive an electrical current from incident electro-magnetic radiation;
   a current integration circuit to
      (i) integrate the electrical current from the photosensor over an integration time interval, and
      (ii) acquire several integration samples of the time-integrated current during the integration time interval; and
   an arithmetic unit to:
      (i) fit the integration samples to a predetermined time dependency of the integrated current,
      (ii) compute an accumulated electrical charge accumulated over the integration time interval from the fit, and
      (iii) supply an output intensity signal that represents the accumulated electrical charge.

2. A detection module as claimed in claim 1, further comprising a synchronization circuit to
   (i) receive a monitor signal that is representative of a disturbance from a disturbance source; and
   (ii) control the operation of the detection module circuit to form the output intensity signal on the basis of the monitor signal.

3. The detection module of claim 2, wherein the synchronization circuit causes the current integration circuit to acquire the integration samples in synchronization with the monitor signal.

4. The detection module of claim 2, wherein the synchronization circuit causes the arithmetic unit to perform a correction on the integration samples in response to the monitor signal.

5. A detection module as claimed in claim 1, wherein the predetermined time dependency of the integrated current is linear.

6. A detection module as claimed in claim 1, wherein the current integration circuit is arranged to acquire a number of integration samples in the range of 400-500 samples.

7. The detection module of claim 1, wherein the current integration circuit continues to integrate the electrical current over the integration time interval until it is reset at the end of the time interval.

8. An apparatus for imaging a turbid medium, comprising:
an examination space to receive the turbid medium;
one or more detection modules placed near the examination space to detect electromagnetic radiation from the turbid medium, the one or more detection modules each being arranged to supply a corresponding output intensity signal representing the detected electromagnetic radiation; and
a reconstruction module to receive the one or more output intensity signals from the one or more detection modules and to reconstruct an image of the turbid medium from the one or more output intensity signals,
wherein each detection module comprises:
 a photosensor to derive an electrical current from the electro-magnetic radiation;
 a current integration circuit to
  (i) integrate the electrical current from the photosensor over an integration time interval, and
  (ii) acquire several integration samples of time-integrated current during the integration time interval; and
 an arithmetic unit to:
  (i) fit the integration samples to a predetermined time dependency of the integrated current,
  (ii) compute an accumulated electrical charge accumulated over the integration time interval from the fit, and
  (iii) supply an output intensity signal that represents the accumulated electrical charge.

9. A method of detection of electro-magnetic radiation, comprising:
deriving an electrical current from incident electro-magnetic radiation;
integrating the electrical current over an integration time interval and acquiring several integration samples of time-integrated current during the integration time interval;
fitting the integration samples to a predetermined time dependency of the time-integrated electrical current;
computing an accumulated electrical charge accumulated over the integration time interval from the fit; and
supplying an output intensity signal that represents the accumulated electrical charge.

10. The method of claim 9, further comprising:
(i) receiving a monitor signal that is representative of a phase of a disturbance source; and
(ii) controlling a current integration circuit to integrate the electrical current in response to the monitor signal.

11. The method of claim 10, wherein the predetermined time dependency of the integrated current is linear.

12. The method of claim 10, wherein controlling the current integration circuit to integrate the electrical current in response to the monitor signal, comprises acquiring the integration samples in synchronization with the monitor signal.

13. The method of claim 10, wherein controlling the current integration circuit to integrate the electrical current in response to the monitor signal, comprises performing a correction on the integration samples in response to the monitor signal.

14. The method of claim 9, further comprising:
continuing to integrate the electrical current over the integration time interval; and
resetting the integration at the end of the time interval.

15. A tangible computer-readable medium having stored thereon instructions for controlling a detection module to:
acquire several integration samples of a time-integrated electrical current during an integration time interval;
fit the integration samples to a predetermined time dependency of the time-integrated electrical current; and
compute an electrical charge accumulated over the integration time interval from the fit of the integration samples to the predetermined time dependency.

16. The tangible computer-readable medium of claim 15, wherein the stored instructions further control the detection module to:
receive a monitor signal that is representative of a phase of a disturbance source; and
control a current integration circuit of the detection module to integrate the electrical current in response to the monitor signal.

17. The tangible computer-readable medium of claim 15, wherein the predetermined time dependency of the integrated current is linear.

* * * * *